United States Patent
Cayemitte-Rückner

(10) Patent No.: US 11,752,066 B2
(45) Date of Patent: Sep. 12, 2023

(54) FIXTURE FOR LIGHT ACUPUNCTURE

(71) Applicant: Naomie Cayemitte-Rückner, Hamburg (DE)

(72) Inventor: Naomie Cayemitte-Rückner, Hamburg (DE)

(*) Notice: Subject to any disclaimer, the term of this patent is extended or adjusted under 35 U.S.C. 154(b) by 342 days.

(21) Appl. No.: 16/811,004

(22) Filed: Mar. 6, 2020

(65) Prior Publication Data
US 2020/0281812 A1 Sep. 10, 2020

(30) Foreign Application Priority Data
Mar. 7, 2019 (DE) ............... 10 2019 105 774.4

(51) Int. Cl.
*A61B 5/00* (2006.01)
*A61H 39/00* (2006.01)
*A61N 5/06* (2006.01)
*A61N 5/067* (2006.01)

(52) U.S. Cl.
CPC ........... *A61H 39/00* (2013.01); *A61N 5/0619* (2013.01); *A61H 2039/005* (2013.01); *A61H 2201/165* (2013.01); *A61H 2205/02* (2013.01); *A61N 5/067* (2021.08); *A61N 2005/063* (2013.01); *A61N 2005/0647* (2013.01)

(58) Field of Classification Search
None
See application file for complete search history.

(56) References Cited

U.S. PATENT DOCUMENTS

| | | | |
|---|---|---|---|
| 6,358,272 B1 | 3/2002 | Wilden | |
| 8,308,784 B2* | 11/2012 | Streeter | A61N 5/0618 128/898 |
| 10,188,872 B2* | 1/2019 | De Taboada | A61N 5/0622 |
| 10,695,579 B2* | 6/2020 | De Taboada | A61N 5/0613 |
| 10,974,047 B2* | 4/2021 | Nelson | A61N 1/36031 |
| 2007/0179571 A1* | 8/2007 | De Taboada | A61N 5/0622 607/88 |
| 2009/0216299 A1 | 8/2009 | Dantus | |
| 2009/0254154 A1* | 10/2009 | De Taboada | A61N 5/0613 607/110 |
| 2010/0204762 A1* | 8/2010 | De Taboada | A61N 5/0613 607/88 |
| 2011/0022132 A1 | 1/2011 | Kim | |
| 2018/0147416 A1* | 5/2018 | Segel | A61H 39/00 |
| 2019/0054311 A1* | 2/2019 | Wasserbauer | A61B 18/203 |
| 2019/0143114 A1* | 5/2019 | Nelson | A61H 39/00 607/3 |
| 2020/0330786 A1* | 10/2020 | De Taboada | A61N 5/0613 |
| 2021/0113853 A1* | 4/2021 | Devens | A61N 5/0622 |
| 2021/0205634 A1* | 7/2021 | Sverdlov | G16H 10/60 |

FOREIGN PATENT DOCUMENTS

EP 0130950 A2 1/1985
JP S60-163943 U 10/1985

* cited by examiner

Primary Examiner — Shirley X Jian
(74) Attorney, Agent, or Firm — HOWSON & HOWSON LLP

(57) ABSTRACT

A fixture for light acupuncture on the head is provided. The fixture has a holding portion extending at least partially over the temporal bone above an ear when being in an attached position. The holding portion has one or several openings through which one optical wave guide each is pluggable so that its front end shining while in operation is attached to the head in the area of the temporal bone.

18 Claims, 2 Drawing Sheets

FIXTURE FOR LIGHT ACUPUNCTURE

BACKGROUND

The invention relates to a fixture for light acupuncture on the head having a holding portion extending at least partially over the temporal bone above an ear of a human and being in an attached position.

The healing effect of traditional acupuncture with needles according to the knowledge of traditional Chinese medical science is generally known. Herein, reflex zones of specific areas of the body are stimulated by needles so that for example detoxication processes are accelerated and the immune system is activated.

Moreover, it is known to stimulate said reflex zones not only by mechanical needles but also by light. At this, laser light is commonly used as light in order to effect desired stimulation.

Light acupuncture or traditional acupuncture have proven of value in particular with chronic disorders. The problem of light acupuncture is that light must act on the chosen reflex zone over a specific period of time. This requires some physician's dexterity and sufficient knowledge. What is more, the light source must then be held on the reflex zone for a specific period of time in order to stimulate it. To this effect, the physician and the patient to be treated must keep calm. Multi-channel laser is available for laser light acupuncture on the body where the light exit source, e. g. an optical wave guide is fastened by means of an adhesive tape over the acupuncture point. This is not readily possible on the head, due to hair.

Experience has shown that good results were obtained by stimulating reflex zones in the area of the ear. It is also known that a multitude of reflex zones exists on the head where various body regions are mapped. Many reflex zones to be treated or acupuncture points are sometimes behind the ear and sometimes above the ear. In the area of the entire temporal bone, there are several reflex zones or acupuncture points effective for said treatment. One treatment of said reflex zones is mastoid acupuncture which has been explored thoroughly by the applicant.

Whereas locating of the known reflex zones is no significant problem, lighting of the chosen reflex zone for light acupuncture purposes over a prolonged period of time is rather laborious for the treating person. Therefore, the object of the invention is to configure a fixture of the type as described hereinabove enabling to conveniently carry out light acupuncture on the head.

The object according to the invention is resolved by the holding portion having one or several openings through which one optical wave guide each is pluggable so that its front end shining while in operation is fitted on the head in the area of the temporal bone. Said generally flexible optical wave guide enables to guide a narrowly limited light beam directly to the chosen reflex zone on the head. Flexibility of the optical wave guide enables the treating physician to conveniently guide light to the chosen spot respectively the chosen spots. Said fixture holds said holding portion in a predetermined manner over the ear so that said optical wave guides can be led through the openings to the desired reflex zones. As soon as said optical wave guide lights the desired reflex zone, the treating physician can choose another reflex point.

Said fixture is finally intended to fasten several optical wave guides to stimulate several reflex zones in the area of the temporal bone so that light can act on said reflex zones even over a prolonged period of time, such as several minutes. Undesirable displacements are reliably avoided by said fixture. Accordingly, only the chosen acupuncture points are actually stimulated. Moreover, the treating physician can leave the patient alone after having attached said fixture.

Basically, said fixture can have a holding portion of the temporal bone on one side. It is nevertheless useful for said fixture to be provided with two holding portions, each extending in its attached position at least partially over the temporal bone on both sides of the head. This enables simultaneous treatment of both sides of the head.

This configuration of said holding portions enables to perfectly hold said optical wave guides in direct contact with the scalp on the head. It is nevertheless useful to hold said optical wave guides in the openings movably to and fro. This enables adjustment of said fixture and length of said optical wave guide facing the head, to various head forms or various situations in the reflex zone area.

According to an advanced embodiment of the invention, it is proved that said optical wave guide is guided in the respective elastically expanded opening and held in the holding portion. This effects a relatively tight fixture of said optical wave guide on said holding portion by simple means so that an optical wave guide is not easily displaced in its opening following its adjustment. Hence, light can very well act on the scalp directly and thereby on the reflex zone.

It is useful for the openings to be arranged in said holding portion in accordance with the mastoid acupuncture reflex points. It has been found that reflex points are fundamentally always arranged in the same position relative to the ear basis, independently from every individual human being. Therefore, it is possible that the holding portion has a predetermined pattern of openings through which said optical wave guides can be guided. Then, the treating physician only needs to choose corresponding openings in order to reach stimulation of desired reflex zones with said optical wave guide.

It is particularly useful that the fixture is designed so that the openings in the holding sections are arranged according to the reflex zones to be treated and to be stimulated behind and/or above the ear. It is therefore provided that the openings are arranged in the holding sections for the treatment of a specific clinical picture.

Thus, it may be expedient that one fixture and the arrangement of the openings in the holding sections is designed for the treatment of, for example, posture problems and another fixture for the treatment of, for example, back pain. This simplifies handling. In particular, an accidental stimulation of incorrect reflex zones is avoided, since the insertion of a fiber optic cable into the wrong opening of the holder is prevented or not possible at all. The fixture has only those openings for fiber optics that are needed to handle one problem. The holder sections are therefore formed as stencils which has only the necessary openings for one possible or desired treatment.

Since the position of the different reflex zones on and above and behind the ear is almost the same for each person, the fixtures can be prefabricated independently of the individual patient. The position of the openings for the stimulation of the selected reflex zones then only has to be aligned relative to the patient's ear.

The applicant has found that the position of the reflex zones relative to the upper and front ear base is almost identical for each person and independent of the size of the person or his head. It is therefore expedient that the fixture or the support sections and the relevant stencils with the openings have a marking with which the holding sections or the stencils are aligned relative to the upper and front ear base. It can be provided, for example, that the holding section has a marking that is in the effective position vertically above the front and upper ear base. The horizontal alignment of the holding sections is caused by a lower edge of the fixture or the holding sections, which rests on the upper ear baseline. For example, the edge can be 1.5 cm to 3 cm long. The openings of the holding sections or the stencils are then aligned according to the selected reflex zones.

Basically, the material the holding portion or the holding portions are made of is discretionary. It is nevertheless useful for said holding portion or holding portions to be made of plastic material and in particular silicone. Silicone offers elastic as well as flexible properties so that it fits well on the patient's head. What is more, silicone can readily be cleaned. But basically, any other elastic and/or flexible plastic material can be used.

It is also useful for the holding portions to be made of transparent material. Then, the treating physician can monitor the right fit of said optical wave guide on the scalp with said fixture attached.

Alternatively, it is possible for the holding portion or the holding portions to be made of textile material. Here, said openings can be constituted such that any desired reflex zone can be reached in the area of the head.

In any case it is useful for said holding portion or holding portions to be movably held on said fixture. This enables to perfectly adjust said fixture to various head shapes or head sizes.

Moreover, it is useful for the holding portion or the holding portions to be removably connected to said fixture. This facilitates cleaning of said fixture as only the removed holding portions must be cleaned and disinfected.

It can be provided that a holding portion extends at least partially behind an ear. Thereby, the reflex zones of the temporal bone covered by the auricle can be charged with light. There, said holding portion also shows through-holes for optical wave guides.

It can also be useful for said optical wave guide to have an extension with through-holes for optical wave guides covering the area below the auricle at the rear ear basis. Said extension can be flexibly connected to the holding portion and be integrally shaped with the latter. But it is also possible that said extension is formed in the area behind the ear as downwards pointing convexity fitted under the auricle at the rear ear basis on the temporal bone in its attached position. Thereby, even reflex zones for mastoid-acupuncture on the temporal bone are covered by simple means and can be reached with optical wave guides arranged behind the ear basis.

For example, said fixture can be configured as a hood in order to cover the entire head area so that said optical wave guides are guidable through openings which are arranged accordingly, to various reflex zones on the head. This enables stimulation by light of reflex zones even outside said temporal bone.

But it is particularly useful for said fixture to be configured as bandeau. Said bandeau's width can be adjustable such that it can easily be adjusted to the head's circumference. Hence, said bandeau extends over the patient's front and occiput so that said holding portions are safely held in the area above the ear. For example, said bandeau can be configured as a rubber flexible or comprise a bandeau adjustable in length.

According to one embodiment of the invention, it is provided that said fixture is configured as a bracket extending over the head and supporting said holding portions on its free ends. Said bracket can press said holding portions in an elastic but sufficiently tight manner to the temporal bone above the ear. Moreover, said bracket can be configured to be adjustable in length so that it is easily adjustable to various head sizes.

In general, said optical wave guides are configured to be elastic and flexible. Hence, it is easily possible to directly position the shining front end on the scalp. The existing distance between said holding portion and said scalp enables to circumvent troublesome hair, for example.

The other ends of the fiber optics can be merged and fed to a common light supply source. High-performance LEDs can be used. It has been shown that high-performance LEDs can produce sufficient but not too high light intensity to stimulate the reflex zones or reflex points. By using LED, the use of the fixture is also harmless.

The stimulation of the periosteum is important during treatment. It is therefore essential that the acting light penetrates only up to the periosteum on the skull. The luminous intensity of the light source used is therefore dimensioned in such a way that a penetration of the light is only caused up to the periosteum on the skull. The light of a stronger light source, such as a laser light source, would penetrate into the brain and act directly on the brain cells which is not desired. It is carried out by the light acting only on the periosteum an irritation or stimulation of the relevant reflex zones, which are located on the periosteum and on which certain body regions are depicted.

By such a fixture or such a holding section or a stencil, the stimulation of the relevant microsystem of the body can take place. The reflex zones or reflex points of the desired microsystem are reliably found through the predetermined openings in the holding sections and can be irritated with light. It can be carried out with the fixture according to the invention an LED light acupuncture and thus a periosteum acupuncture of predetermined reflex zones in the area of the temple leg is comfortable and safe for a longer period of time for the treating physician.

Moreover, it can be provided that said light shines in various wave lengths. Said wave lengths can either be discretionarily selectable or be changed automatically. Pulsed light can also be used. Finally, this is at the treating physician's discretion.

BRIEF DESCRIPTION OF THE DRAWINGS

Hereinafter, the invention will be explained in more details by way of the schematic drawings, wherein.

DETAILED DESCRIPTION

Figure 1:
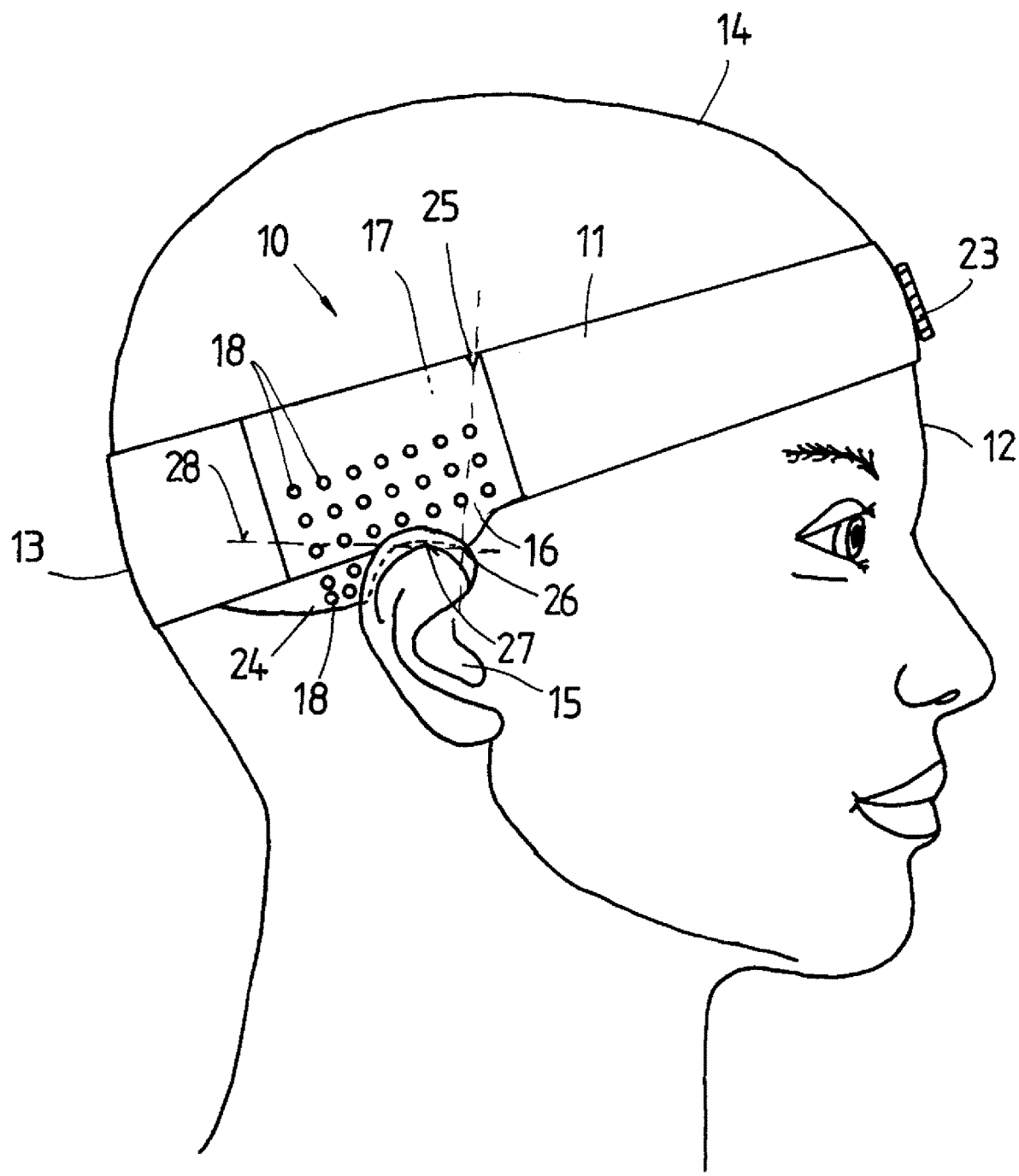
FIG. 1 shows the lateral view of a head with a fitted fixture according to the invention.
Figure 2:
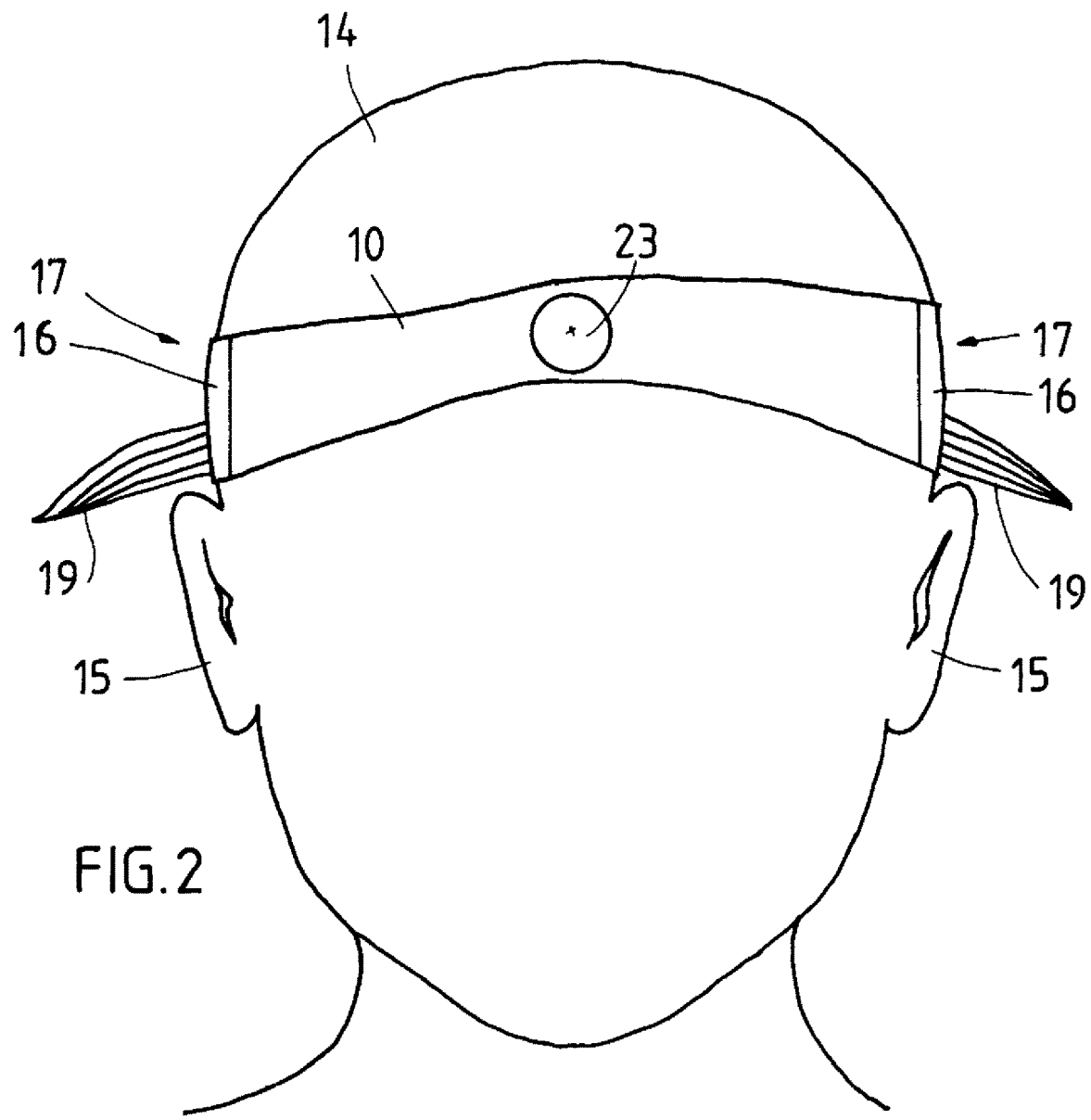
FIG. 2 shows the front view of a head with a fitted fixture.
Figure 3:
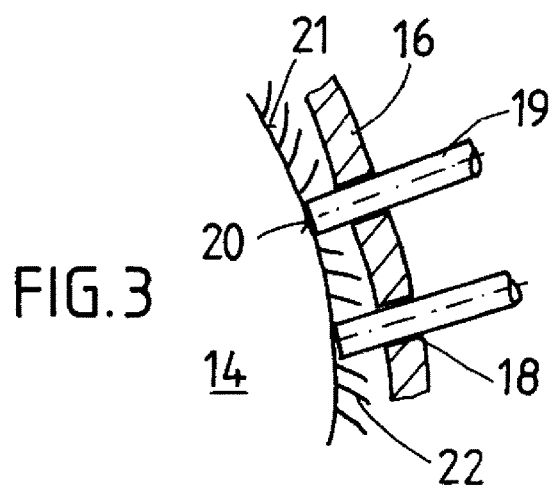
FIG. 3 shows a cut-out view through the holding portion in the area of the openings.

The fixture 10 shown in the drawing for light acupuncture purposes is configured as a bandeau 11 extending over the front area 12 and the occiput 13 of the head 14 of a human being. Hence, said bandeau 11 approximately has the aspect of a headband.

In the area above an ear 15, said fixture 10 has a holding portion 16 extending over said temporal bone 17 above said ear 15 on each side. Thereby, said temporal bone 17 of the head 14 is covered at least partially. Openings 18 suitable enable passing through of said optical wave guides 19 are provided in said holding portion 16. In detail, the arrangement is configured as to hold said optical wave guides 19 relatively tight in the openings 18 so that they are movable to and fro towards the friction force. Thereby, said optical wave guides 19 respectively their free front sides 20 which shine in operation can perfectly be fitted to the scalp 21 of the head 14. Owing to frictional guidance of the optical wave guide 19 in the allotted opening 18, any move back of said optical wave guide, for example due to a movement of the head, is reliably prevented.

Said openings 18 are arranged on the holding portion 16 such that, in an attached position, they are essentially positioned over the known mastoid acupuncture reflex zones on the temporal bone 17 of the head 14 and in particular above and partially behind the ear 15 of a human being. Said optical wave guide 19 is held vertically relative to said holding portion 16 in said openings 18 so that the free front end 10 is safely attached to the scalp 21. The optical wave guide diameter is chosen such that said optical wave guide can perfectly be positioned between hair 22 and directly on the scalp 21. Hence, light can directly act on the scalp and thereby on the reflex zones of the temporal bone 17.

The optical wave guide 19 diameter comes for example to 1.5 mm to 5 mm, in particular to 2 mm to 3 mm. The free front ends 20 of the optical wave guides 19 can be configured to be plane. For comfortable wearing, the front ends 20 can also be configured to be round. It is at least useful for the edges to be round in order to avoid any uncomfortable pressure on the scalp.

In the embodiment shown, said bandeau 11 is tightly connected to the holding portions 16. It is in particular provided for said bandeau 11 and the holding portions 16 on both sides to be made of plastic material. In particular in the holding portions 16, said plastic material has a thickness sufficient to safely guide the passed through optical wave guide 19 in said openings 18. Thereby, any bending down or any undesirable inclined course of said optical wave guide 19 relative to said holding portion 16 is avoided. For example, thickness of said holding portions 16 can be 3 to 8 mm.

But said bandeau 11 can also removably be connected to said holding portions 16. Then, said bandeau 11 can be made of a rubber flexible material so that said holding portions can perfectly and independently from the actual head size be held in the desired position over the ear.

But it can also be provided that, in case of configuration in one piece of said fixture 10, an adaption mechanism 23 is provided intended to enable adjustment of the width of said bandeau 11. Such adaption mechanisms are basically known and therefore require no additional description.

Basically, it is provided that said holding portions 16 extend over an ear 15. But it can also be provided that said holding portions 16 have, in the area of the rear ear basis, one extension 24 each with through holes 18 and which, in its attached position, is at least partially fitted below the auricle on the temporal bone 17. This enables said optical wave guide's 19 orientation relative to the reflex zones on the entire temporal bone.

Said optical wave guides can have a diameter of 1.5 mm to 5 mm and in particular of 2 mm to 3 mm, thereby enabling to be perfectly guided to the scalp, passing through the hair. Hence, light exiting on the free front end 20 can directly act on the scalp 21 and the acupuncture points. Several optical wave guides 19 intended to treat several reflex zones can be arranged on one holding portion 16. It is useful for said optical wave guides 19 to be guided in bundles at a distance from said holding portion 16 and in a consolidated form to a light source (not shown). Said light source can, for example, be positioned at a distance of 0.8 to 2.0 meters relative to said fixture such that comfortable fitting and wearing of such fixture 10 are possible.

Detailed configuration of said optical wave guides is basically known and does not require any further description. One or more high-power LEDs able to emit light with various wave lengths can be used as light sources. Hence, it is possible to stimulate said reflex zones by various wave lengths.

Said fixture is bound to be fitted easily to the head of a human being. This can be realised either by trained professionals or by the patient him-/herself. Orientation of said optical wave guides on said reflex zones can be ensured individually. Here, it can be provided that a fixture with openings is provided in the reflex zones relevant to a patient. But it can also be provided that said openings 18 are arranged alongside a pattern such that said optical wave guide is guided through the desired opening to the desired reflex zone, where said fixture is attached. Altogether, this enables to guide a sufficient amount of light directly to said reflex zone. Moreover, it is possible for said optical wave guide to remain on the same reflex zone over a prolonged period of time of, e. g., 5 to 20 minutes and in particular 7 to 15 minutes so that said reflex zone is stimulated over a sufficient period of time.

However, it can also be provided that the holding sections 16 have prefabricated openings 18 for the treatment of certain clinical pictures. The openings are then located in the applied position of the fixture above the selected reflex points for the treatment of the relevant clinical picture. In order that the fixture and the retaining sections 16 and thus the openings 18 can be correctly aligned to the ear 15 of the patient, the fixture 10 has a mark 25 which is aligned in the correct position of the fixture 10 vertically or cranial above the front and upper ear base 26. The marking 25 can be formed as a notch or a protrusion.

The horizontal alignment can be done via a horizontal bottom edge 27 of the fixture or the holding sections 16, which is supported in the correct position of the fixture 10 on the upper horizontal ear base line 28. Thus, an exact alignment of the fixture or its holding sections 16 relative to the ear 15 is possible. By the elastic design of the band 11, the fixture can be adjusted to different head sizes with the same orientation of the holding sections 16 relative to the respective assigned ear.

The invention claimed is:

1. An assembly for light acupuncture on a head of a patient, comprising:
   a fixture having a holding portion which in its attached position extends at least partially over a temporal bone above an ear of the patient, wherein said holding portion has one or several opening(s), which opening(s) are arranged in accordance with mastoid acupuncture reflex points of the temporal bone above the ear of the patient;
   an optical wave guide that is pluggable into the opening(s), such that, when the fixture is in an operating position when worn on the head of the patient, a front end of the optical wave guide which front end is shining in operation is guided through the opening(s) to directly shine light on the mastoid acupuncture reflex points on an area of the temporal bone above the ear of the patient in order to stimulate said mastoid acupuncture reflex points; and a light source to which an opposite end of the optical wave guide is connected, the light source emits light of a luminous intensity dimensioned such that penetration of light into the head of the patient is only caused up to the periosteum of a skull of the patient.

2. The assembly according to claim 1, wherein the fixture has two holding portions, such that when the fixture is in an operating position when worn on the head of the patient, the holding portions are positioned to extend at least partially over the temporal bones on both sides of the head of the patient.

3. The assembly according to claim 2, wherein said optical wave guide and the opening(s) are sized such that the optical wave guide is held by and movable back and forth in said opening(s).

4. The assembly according to claim 3, wherein, when said optical wave guide is guided in the opening(s), the optical wave guide is held in the opening(s) by elastic compression or friction and therefore held in one of the holding portions.

5. The assembly according to claim 4, wherein said holding portions are made of plastic material.

6. The assembly according to claim 5, wherein said holding portions are made of transparent material or silicone.

7. The assembly according to claim 6, wherein said holding portions are movably held on or movably connected to said fixture.

8. The assembly according to claim 7, wherein each of said holding portions includes an extension with through-holes arranged to cover an area below the auricle at the rear ear basis of the patient when the fixture is worn by the patient.

9. The assembly according to claim 1, wherein the fixture is configured as a hood that covers the entire head area of the patient when the fixture is worn by the patient so that said optical wave guide is guidable through the opening(s).

10. The assembly according to claim 1, wherein the fixture is configured as a bandeau.

11. The assembly according to claim 1, wherein said optical wave guide and the opening(s) are sized such that the optical wave guide is held by and movable back and forth in said opening(s).

12. The assembly according to claim 1, wherein, when said optical wave guide is guided in the opening(s), the optical wave guide is held in the opening by elastic compression or friction and therefore held in the holding portion.

13. The assembly according to claim 1, wherein said holding portion is made of plastic material.

14. The assembly according to claim 1, wherein said holding portion is made of transparent material or silicone.

15. The assembly according to claim 1, wherein said holding portion is movably held on or connected to said fixture.

16. The assembly according to claim 1, wherein said holding portion includes an extension with through-holes arranged to cover an area below the auricle at the rear ear basis of the patient when the fixture is worn by the patient.

17. The assembly according to claim 1, wherein the light source is a LED.

18. The assembly according to claim 1, wherein the optical wave guide has a diameter of 1.5 mm to 5 mm.

* * * * *